United States Patent [19]

Sih

[11] Patent Number: 4,642,290
[45] Date of Patent: Feb. 10, 1987

[54] PROCESS FOR PREPARING A COMPOUND FOR USE IN THE PRODUCTION OF L-CARNITINE

[76] Inventor: Charles J. Sih, 6322 Landfall Dr., Madison, Wis. 53705

[21] Appl. No.: 447,171

[22] Filed: Dec. 6, 1982

[51] Int. Cl.$^4$ .................. C12P 13/00; C12P 13/02; C12P 7/52; C12P 7/62
[52] U.S. Cl. .................... 435/128; 435/129; 435/141; 435/135
[58] Field of Search ............... 435/128, 135, 141, 280, 435/942, 129, 911, 912, 913, 916, 921, 922, 923, 930, 931, 933, 934, 937, 938, 939, 940, 943, 945

[56] References Cited

U.S. PATENT DOCUMENTS 3,823,069  7/1974  Miyaki .................... 435/280
3,925,156  12/1975 Chang et al. ............. 435/135
4,211,846  7/1980  Lafferty ................. 435/829 X
4,371,618  2/1983  Cavazza ................. 435/128

FOREIGN PATENT DOCUMENTS 2268787  11/1975  France .
0118438   9/1980  Japan ................... 435/141
0111691   7/1983  Japan ................... 435/141
0155094   9/1983  Japan ................... 435/135

OTHER PUBLICATIONS

Sih et al., "Strategies for Controlling the Stereochemical Course of Yeast Reductions", in: Selectively—A Goal for Synthetic Efficiency, Fourteenth Workshop Conference, Schloss, Reisenburg, Sep. 18–22, 1983; Verlag Chemie, Weinheim, Germany, (1984), pp. 251–261.
Morrison et al., Organic Chemistry, third edition, Boston, Allyn and Bacon, Inc., 1973, p. 1089.
Chemical Abstracts, vol. 84, 1976, Abstract No. 59999, Tenud.
Mori, Tetrahedron, vol. 37, (1981), pp. 1341–1342.
Limieux et al., Can. J. Chem., vol. 29, (1951), pp. 678–690.
Frater, Helvetica Chimica Acta, vol. 62, (1979), pp. 2829–2832.
Hirama et al., J. Am. Chem. Soc., vol. 104, (1982), pp. 4251–4253.
Zhou et al., J. Am. Chem. Soc., vol. 105, pp. 5925–5926, (1983).
Hirama et al., J. Chem. Soc., Chem. Commun., (1983), pp. 599–600.
Nakamura et al., Tetrahedron Letters, vol. 25, No. 36, (1984), pp. 3979–3982.
Fuganti et al., Tetrahedron Letters, vol. 26, No. 1, (1985), pp. 101–104.
Seebach et al., Angew. Chem. Int. Ed. Engl., vol. 23, (1984), No. 2, pp. 151–152.
*Chemical Abstracts*, vol. 99, 1983, Abstract No. 103632f, Zhou et al.
S. Deol et al., *Aust. J. Chem.* (1976), 29,2459.
Chem. Abst., 78 (1973), 147382v.
Chem. Abst., 75 (1971), 19716h.

*Primary Examiner*—David M. Naff
*Assistant Examiner*—Randall E. Deck
*Attorney, Agent, or Firm*—Isaksen, Lathrop, Esch, Hart & Clark

[57] ABSTRACT

A process for preparing L-carnitine which comprises exposing γ-substituted acetoacetic acid esters or amides to the fermentative enzymatic action of a microorganism which elaborates oxido-reductase enzymes, recovering the resulting, optically active, corresponding γ-substituted-β-hydroxybutyric acid derivative and converting said derivative to L-carnitine.

16 Claims, No Drawings

PROCESS FOR PREPARING A COMPOUND FOR USE IN THE PRODUCTION OF L-CARNITINE

FIELD OF THE INVENTION

The concept of the present invention has been set forth in Disclosure Document No. 111285.

This invention relates to a process for producing key chiral intermediates for L-carnitine synthesis. Specifically, it relates to a microbiological process for asymmetrically reducing the beta-keto group of 4-substituted acetoacetic esters and amines into their respective 4-substituted 3-hydroxybutyric acid derivatives of the L-configuration (exhibiting the R-configuration, according to the designation of Cahn-Ingold-Prelog). This was accomplished by altering the steric course of microbial reduction using 4-substituted acetoacetic substrates bearing large hydophobic ester or amine moieties. The resulting 4-substituted 3-hydroxybutyric acid derivatives of the desired absolute configuration (L or R) readily can be converted into L-carnitine chloride by reaction with trimethylamine.

BACKGROUND OF THE INVENTION

As is well known, carnitine ($\beta$-hydroxy-$\gamma$-trimethyl-amino butyric acid) contains a center of asymmetry and therefore, carnitine exists in two stereoisomeric forms, the D and the L forms.

L-carnitine is normally present in the body where it functions to carry activated long-chain free fatty acids through the mitochondrial membrane. Since the mitochondrial membrane is impermeable to acyl CoA derivatives, long-chain free fatty acids can enter only when esterification with L-carnitine has taken place. The carrier function of L-carnitine is exerted both by transporting active long-chain fatty acids from the sites of their bio-synthesis, for the example the microsomes, to the mitochondria where they are oxidized, and by transporting acetyl CoA from the mitochondria, wherein it is formed, to the extramitochondrial sites where the synthesis of long-chain fatty acids occurs, e.g., in the microsomes wherein acetyl CoA can be utilized for synthesizing cholesterol and fatty acids.

While it has been established that the laevorotatory isomer (L-carnitine) exclusively is the biological form (D-carnitine has never been detected so far in mammalian tissues), the D,L-carnitine racemate has been used for a number of years for different indications. For example, D,L-carnitine is sold in Europe as an appetite stimulant, and it has been reported that the material has an effect on the growth rate of children; see e.g., Borniche et al., Clinica Chemica Acta, 5, 171–176, 1960 and Alexander et al., "Protides in the Biological Fluids", 6th Colloquim, Bruges, 1958, 306–310. U.S. Pat. No. 3,830,931 describes improvements in myocardial contractility and systolic rhythm in congestive heart failure which can often be obtained through administration of D,L-carnitine. U.S. Pat. No. 3,968,241 describes the use of D,L-carnitine in cardiac arrhythmias. U.S. Pat. No. 3,810,994 discloses the use of D,L-carnitine in the treatment of obesity.

Recently, however, there has been an increasing emphasis on the importance of utilizing exclusively the carnitine laevorotatory isomer for at least some therapeutic applications. It has, in fact, been shown that D-carnitine is a competitive inhibitor of carnitine-linked enzymes such as carnitine acetyl transferase (CAT) and carnitine palmityl transferase (PTC). Moreover, recent evidence suggests that D-carnitine can deplete the L-carnitine level of heart tissue. Consequently, it is essential that L-carnitine exclusively be administered to patients under medical treatment for heart diseases or lowering of blood lipids.

Several processes have been proposed for producing carnitine on an industrial scale. The chemical synthesis of carnitine unavoidably leads, however, to a racemic mixture of the D and L isomers. Consequently, resolution methods have to be employed to obtain the separate optical antipodes from the racemate.

A typical resolution method wherein D,L-carnitinamide hydrochloride is used as the starting compound for resolution is disclosed in Belgian Pat. No. 660039. Such process comprises the use of D-camphoric acid for producing the D-camphorate of D,L-carnitinamide. An alcoholic solution of this compound is subjected to fractional crystallization so as to give the L-isomer as the first fraction to precipitate from the solution.

In order to form the D-camphorate of D,L-carnitinamide, it is first necessary to form the ammonium salt of D-camphoric acid with ammonia; the ammonium D-camphorate that is formed is then converted to silver D-camphorate by the action of silver nitrate. Since the carnitinamide is in the hydrochloride salt form, the formation of this silver salt is essential in order to eliminate the chloride ion. Such a process is, therefore, very expensive (because of the imperative use of the silver compound) and difficulty to carry out industrially in that the various steps of the process have to be carried out away from the light in order to avoid marked blackening of the reaction vessels, due to the large quantity of AgCl which is formed. The D-camphorate of D,L-carnitinamide may, in addition, be rendered impure by the presence of silver ions.

Moreover, after the D-camphorate of L-carnitinamide has been crystallized out of the alcoholic solution, further steps are needed to eventually convert it into L-carnitine.

DESCRIPTION OF THE INVENTION

It is an object of this invention to produce L-carnitine chloride in good yield through a combination of microbiological and chemical processes. The advantages of this invention will be apparent to those skilled in the art from the following detailed description.

That the $\beta$-keto function in the 3-position in the $\gamma$-substituted-acetoacetic acid derivatives can be reduced by hydrogenation over Pt/C is known (e.g., U.S. Pat. No. 3,969,406). However, the hydroxy compound resulting from such method is racemic. In contrast, by employing the fermentative action of a microorganism in accordance with the process of the present invention, the hydrogenation of the oxo-function at the 3-position can be accomplished stereoselectively to yield the 3(R) or L epimeric configuration. This configuration is required for the conversion into the natural L-carnitine.

Broadly this invention comprises the use of microbial reductases to catalyze stereoselective hydrogenation of $\gamma$-substituted acetoacetic acid derivatives having the formula: $XCH_2COCH_2COR$, where X is Cl, Br or OH and R is any hydrophobic group which will bind to the active site of the enzyme. For example, R can be an alkyl alcohol or amine grouping having from about 5 to about 15 carbon atoms, alicyclic alcohol or amine groupings having from about 5 to about 12 carbon atoms, aromatic alcohols having from about 6 to about 14 carbon atoms and containing, optionally, substituents such as H, CH$_3$, halo, or nitro groups on the rings, aromatic amines having the formulas:

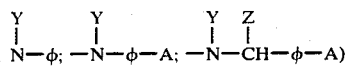

where Y and Z=H, alkyl (C$_1$–C$_8$), phenyl or benzyl and A=H, CH$_3$, Cl, Br. It will be obvious to those skilled in the art that for the purposes of this invention the substituent designated as R in the above acetoacetic-system can vary widely. Thus, it can be a a substituted or unsubstituted, ester or amide grouping, and it can be aliphatic, cyclic or aromatic in nature, or can comprise any mixture thereof so long as the particular R group selected permits the compound to be hydrogenated by a microorganism.

It has been found that the microorganisms which are capable of functioning to catalyze the stereoselective reduction described above are those which elaborate oxido-reductase enzymes. Particularly suitable are those microorganisms of the class Ascomycetes and the orders Endomycetales, Mucorales, Moniliales and Eurotialis.

The γ-substituted-R-β-hydroxybutyric acid derivatives resulting from the microbial reduction of the γ-substituted acetoacetic acid derivatives is then reacted with trimethylamine to yield the corresponding γ-trimethylammonium-R-β-hydroxybutyric acid derivative, which can be readily converted into L-carnitine by treatment with aqueous acids. The following is a schematic of the reaction steps of this invention.

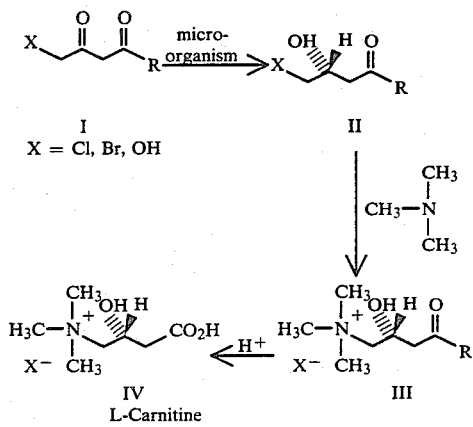

Microorganisms which are characterized by their oxido-reductase activity are well known in the microbiological art and any of such microorganisms can be employed in conducting the process of the present invention (See, K. Kieslich, "Microbial Transformations of Non-Steroid Cyclic Compounds" (Georg Thieme Publishers, Stuttgart, 1976)) with any of the genera of microorganisms specifically described herein being particularly applicable. Readily available and inexpensive microorganisms of the genera Saccharomyces, e.g., brewer's yeast, baker's yeast and winemaker's yeast (*Sacharomyces vini*) have been found to be eminently advantageous in carrying out the process of the invention.

The γ-substituted-acetoacetic substrate can be incorporated in a nutrient medium of standard composition in which such organisms are cultivated and the usual conditions of fermentation can then be employed to effect the reductive transformation. Alternatively, the active principle can be removed from the growing culture of the microorganism, for instance by lysis of the cells to release the enzymes, or by suspension of the resting cells in a fresh aqueous system. In any of these techniques the 1-keto function will be selectively reduced, so long as the active principle elaborated by the microorganisms is present in the medium. Of course, the temperature, time and pressure conditions under which the contact of the γ-substituted-acetoacetic derivative with the reductive principle is carried out are interdependent as will be apparent to those skilled in the art. For instance, with gentle heating and at atmospheric pressure the time required to effect the reductive conversion will be less than if it progresses at room temperature under conditions otherwise the same. Of course, neither temperature, nor pressure, nor time, should be so great that it results in the substrate being degraded. Where a growing culture of the organism is being used, the process conditions should also be sufficiently gentle so the organism is not killed before it elaborates sufficient hydrolytic enzymes to permit the reacton to proceed. Generally, at atmospheric pressure, the temperature can range from about 10° C. to about 35° C., and the time from about 12 hours to about 10 days.

In the following examples which are presented to illustrate this invention and are not to be construed as limiting the scope of the appended claims, the γ-halo acetoacetic acid derivative substrates to be subjected to microbiological reduction were prepared from diketene according to the general method of C. D. Hurd and H. L. Abernethy (J. Am. Chem. Soc., 62, 1147, 1940) for the γ-chloro-acetoacetic derivatives and F. Chick, N. T. M. Wilsmore [J. Chem. Soc., 1978 (1910)] for the γ-bromo-acetoacetic derivatives via the following reaction sequence:

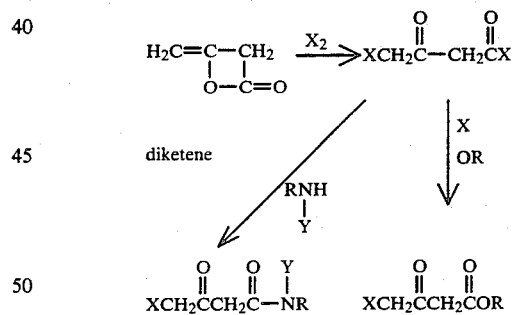

where
X=Cl or Br
Y=H or alkyl
R=as defined previously

Alternatively, if desired, the γ-halo acetoacetic acid derivatives can be prepared from γ-halo acetic esters via a conventional Grignard reaction. For example, γ-chloro acetoacetic octyl ester was readily prepared by refluxing γ-chloro octyl ester with two equivalents of magnesium in ether for 48 hours. After removal of the solvent the acetoacetic octylester was recovered in about 70% yield.

γ-Hydroxy acetoacetic acid derivatives were prepared from their corresponding γ-bromoacetoacetic acid derivatives by stirring in a dioxane-water (1:1) solution containing CaCO$_3$ at 25° C. for 12 hours.

Each of the products produced in accordance with the following examples was identified as to structure through the use of nuclear magnetic resonance (nmr), infrared spectra, and by thin layer chromatographic mobilities. The optical purity and the absolute configuraton of the products were established by their conversion into L-carnitine as well as by conversion into their esters which are readily analyzed by nmr spectrometry, and optical rotation.

EXAMPLE 1 (Yeasts)

(+)4-Chloro-3(R)-hydroxybutyric acid octyl ester was prepared as follows:

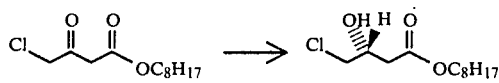

A. Fermentation

Surface growth from a one week old agar slant of *Candida keyfr.* NRRL Y-329, grown on agar of the following composition:

|  | Gms |
|---|---|
| Agar | 20 |
| Glucose | 10 |
| Yeast extract | 2.5 |
| K$_2$HPO$_4$ | 1 |
| Distilled water, q.s. 1 liter | |
| (Sterilized 15 min at 20 p.s.i.) | | was suspended in 5 ml of an 0.85% saline solution. One ml portions of this suspension were used to inoculate a 250 ml Erlenmeyer flsk (F-1 stage) containing 50 ml of the following medium (Vogel's medium):

|  | Gms |
|---|---|
| Yeast extract | 5 |
| Casamino acids | 5 |
| Dextrose | 40 |
| Na$_3$—citrate-5½H$_2$O | 3 g |
| KH$_2$PO$_4$ | 5 g |
| NH$_4$NO$_3$ | 2 g |
| CaCl$_2$.2H$_2$O | 0.1 g |
| MgSO$_4$.7H$_2$O | 0.2 g |
| Trace element solution | 0.1 ml |
| Distilled water, q.s. 1 liter | |
| pH 5.6 (sterilized for 15 min at 30 p.s.i.) | |

| Trace element solution | Gm/100 ml |
|---|---|
| Citric acid-1H$_2$O | 5 |
| ZnSO$_4$.7H$_2$O | 7 |
| Fe(NH$_4$)$_2$(SO$_4$)$_2$.6H$_2$O | 1 |
| CuSO$_4$.5H$_2$O | 0.25 |
| MnSO$_4$.1H$_2$O | 0.05 |
| H$_3$BO$_3$ | 0.05 |
| NaH$_2$MoO$_4$.2H$_2$O | 0.05 |

The flask was incubated at 25° C. on a rotary shaker (250 cycles/min—2" radius) for 24 hours, after which a 10% by volume transfer was made to another 250 ml Erlenmeyer flask (F-2 stage) containing 50 ml of Vogel's medium. After 24 hours of incubation on a rotary shaker, 150 mg of γ-chloroacetoacetic acid octyl ester in 0.1 ml of 10% Tween 80 was added. The F-2 stage flask was then incubated for an additional 24 hours under the conditions used in the incubation of the F-1 stage flasks.

B. Isolation

Twenty-four hours after the addition of the γ-chloroacetoacetic acid octyl ester, the cells were removed by centrifugation. The supernatant was exhaustively extracted with 50 ml of ethyl acetate three times. The ethyl acetate was dried over Na$_2$SO$_4$ and evaporated to afford an oily residue (186 mg). The residue was dissolved in 0.5 ml of the mobile phase and added onto a column (1×25 cm) of silica gel (MN-kieselgel 60). The column was eluted with Skelly B:ethyl acetate (8:1) and 14 ml fractions were collected. Fractions 6 and 7 containing the desired product were pooled and concentrated to dryness yielding 120 mg of crystalline residue. Recrystallization from ethyl acetate-hexane afforded 107 mg of 4-chloro-3(R)-hydroxybutyric acid octyl ester, $[\alpha]_D^{23}$ +13.3° (c, 4.45) (CHCl$_3$); pmr (δ CDCl$_3$) 0.88 [3H, tr. distortional, CH$_3$—(CH$_2$)$_n$—]; 1.28 [10H, s, —(CH$_2$)$_5$—]; 1.65 (2H, m,

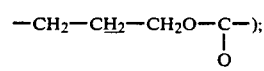

2.62 (2H, d, J=6 Hz,

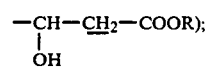

3.22 (1H, br., —O$\underline{H}$); 3.60 (2H, d, J=6 Hz,

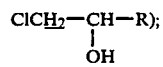

4.20 (3H,

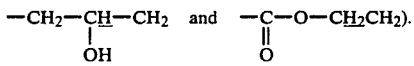

Anal. calcd for C$_{12}$H$_{23}$O$_3$Cl: C, 57.47; H, 9.25. Found: C, 57.52; H, 9.07. [TLC R$_f$—0.5, Brinkmann silica gel plate, 0.25 cm EM; Skelly B:ethyl acetate (5:1).]

EXAMPLE 2

Resting Cells

One hundred grams of commercial fresh Baker's yeast *Saccharomyces cerevisiae* (Red Star) was suspended in 250 ml of tap water to which was added 10 g of sucrose and 3.6 g of γ-chloroacetoacetic octyl ester. After the contents were incubated at 25° C. on a rotary shaker (250 cycles/minute—2" radius) for 24 hours, an additional 10 g of sucrose was added to the flask and the reaction was allowed to proceed for another 24 hours. The cells were then removed by filtration through a pad of celite. The cells were washed with water and ethyl acetate. The washings were combined with the filtrate and exhaustively extracted with ethyl acetate. The ethyl acetate layer was dried over MgSO$_4$ and evaporated to give an oily residue, which was chromatographed over a silica gel column to yield 2.52 g of 4-chloro-3(R)-hydroxybutyric acid octyl ester, as a low melting solid; $[\alpha]_D^{23}$ +13.2° (c, 4.0, CHCl$_3$).

EXAMPLE 3

(+)4-Chloro-3(R)hydroxybutyric acid benzyl ester was prepared as follows:

A. Fermentation

Surface growth from a one week old agar slant of *Gliocladium virens* ATCC 13362, grown on agar of the following composition:

|  | Gms |
|---|---|
| Malt extract | 20 |
| Glucose | 20 |
| Peptone | 1 |
| Agar | 20 |
| Distilled water, q.s. 1 liter | |
| (Sterilized 15 min at 20 p.s.i.) | | was suspended in 5 ml of an 0.85% saline solution. One ml portions of this suspension were used to inoculate a 250 ml Erlenmeyer flask (F-1 stage) containing 50 ml of the following medium (Soybean dextrose medium):

| Soybean meal | 5 g |
|---|---|
| Dextrose | 20 g |
| NaCl | 5 g |
| KH$_2$PO$_4$ | 5 g |
| Yeast | 5 g |
| Water | 1 l |
| pH adjusted to 7.0 | |
| Autoclave at 15 p.s.i. for 15 minutes | |

The flask was incubated at 25° C. on a rotary shaker (250 cycles/min—2" radius) for 24 hours, after which a 10% by volume transfer was made to another 250 ml Erlenmeyer flask (F-2 stage) containing 50 ml of soybean dextrose medium. After 24 hours of incubation on a rotary shaker, 150 mg of γ-chloroacetoacetic benzyl ester in 0.1 ml of 10% Tween 80 was added. The F-2 stage flask was then incubated for an additional 24 hours under the conditions used in the incubation of the F-1 stage flasks.

B. Isolation

Twenty-four hours after the addition of the γ-chloroacetoacetic benzyl ester, the mycelia were removed by filtraton. The filtrate was exhaustively extracted with 50 ml of ethyl acetate three times. The ethyl acetate layer was dried over MgSO$_4$ and concentrated in vacuo to yield a residue (160 mg). The residue was chromatographed over a silica gel (MN-Kieselgel 60) column (1×25 cm). The column was eluted with Skelly B and ethyl acetate (10:1) and 12 ml fractions were collected. Fractions 11–16 containing the desired product were pooled and concentrated to dryness to afford 115 mg of 4-chloro-3(R)-hydroxybutyric acid benzyl ester, $[\alpha]_D^{23} + 8.7°$ (c, 5.26; CHCl$_3$); pmr (δCDCl$_3$) 2.65 (2H, d, J=6 Hz,

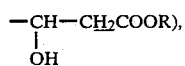

3.20 (1H, br, —O$\underline{H}$); 3.54 (2H, d, J=6 Hz,

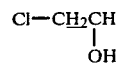

4.20 (1H, m,

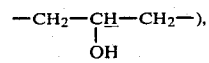

5.12 (2H, s,

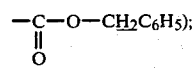

7.31 (5H, s, five aromatic protons). Anal.calcd.for C$_{11}$H$_{13}$O$_3$Cl: C, 57.77; H, 5.73. Found: C, 57.64; H, 5.67. [TLC silica gel EM Brinkmann plate, 0.25 cm, R$_f$=0.43, Skelly B-ethyl acetate (5:1).]

EXAMPLES 4–23

The procedure of Example 1 was repeated with each of the organisms listed in Table 1 except that γ-chloroacetoacetic acid octyl ester was added at a concentration of 1 mg/ml. Conversion to the desired product (+)4-chloro-3(R)-hydroxybutyric acid octyl ester was obtained.

EXAMPLES 24–48

The procedure of Example 3 was repeated with each of the organisms listed in Table 2 except that γ-chloroacetoacetic acid octyl ester (1 mg/ml) was used. Transformation to the desired compound (+)4-chloro-3(R)-hydroxybutyric acid octyl ester was obtained.

EXAMPLES 49–68

The procedure of Example 1 was repeated with each of the organisms listed in Table 1 except that γ-chloroacetoacetic acid benzyl ester (1 mg/ml) was used as the substrate. Conversion to the desired product (+)4-chloro-3(R)-hydroxybutyric acid benzyl ester was obtained.

EXAMPLES 69–93

The procedure of Example 3 was repeated with each of the organisms listed in Table 2 using γ-chloroacetoacetic acid benzyl ester (1 mg/ml) as substrate. Transformation to the desired compound (+)4-chloro-3(R)-hydroxybutyric acid benzyl ester was obtained.

EXAMPLE 94

(+)4-Chloro-3(R)-hydroxybutyric acid anilide was prepared in accordance with the procedure of Example 2 except that γ-chloroacetoacetanilide was used at a concentration of 1 mg/ml

as the substrates for the conversion into the desired optically-active product, m.p. 110°–111° C.; $[\alpha]_D^{23} + 17.5°$ (c, 3.0, CHCl$_3$); pmr

2.67 (2H, d, J=6 Hz, —HOHCH₂—CONHR), 3.66 (2H, d, J=6 Hz, ClCH₂CHOH—R), 4.43 (1H, m, —CH₂—CHOH—CH₂—), 7.03–7.44 (3H, m, aromatic protons, meta and para), 7.69 (2H, d, J=6 Hz, aromatic protons, ortho), 9.24 (1H, br,

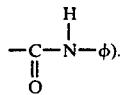

Anal. calcd for C₁₀H₁₂NO₂Cl: C, 56.21; H, 5.66. Found: C, 56.17; H, 5.47.

EXAMPLES 95–114

The procedure of Example 1 was repeated with each of the organisms listed in Table 1 except that γ-chloroacetoacetanilide was added at a concentraion of 1 mg/ml. In all cases conversion to the desired product, (+)4-chloro-3(R)-hydroxybutyric acid anilide was obtained.

EXAMPLES 115–139

The procedure of Example 3 was repeated with the organisms listed in Table 2. γ-Chloroacetoacetanilide was introduced at a concentration of 1 mg/ml. In these cases, conversion to the desired (+)4-chloro-3(R)-hydroxybutyric acid anilide was achieved.

EXAMPLES 140–159

The procedures of Example 1 was repeated with the organisms listed in Table 1 except tht γ-bromoacetoacetic acid octyl ester (1 mg/ml) was used as the substrate. Conversion to the desired produt, (+)4-bromo-3(R)-hydroxybutyric acid octyl ester was obtained.

EXAMPLES 160–184

The procedure of Example 3 was repeated with the organisms listed in Table 2 except that γ-bromoacetoacetic acid octyl ester (1 mg/ml) was used. Conversion to the desired product, (+)4-bromo-3(R)-hydroxybutyric acid octyl ester was obtained.

EXAMPLES 185–204

The procedure of Example 1 was repeated with the organisms listed in Table 1 except that γ-bromoacetoacetic acid benzyl ester (1 mg/ml) was used as the substrate. Conversion to the desired product, (+)4-bromo-3(R)-hydroxybutyric acid benzyl ester was obtained.

EXAMPLES 205–229

The procedure of Example 3 was repeated with the organisms listed in Table 2 except that γ-bromoacetoacetic acid benzy ester (1 mg/ml) was used. Conversion to the desired product, (+)4-bromo-3(R)-hydroxybutyric acid benzyl ester was obtained.

EXAMPLES 230–249

The procedure of Example 1 was repeated with the organisms listed in Table 1 except that γ-bromoacetoacetanilide (1 mg/ml) was used as the substrate. Conversion to the desired (+)4-bromo-3(R)-hydroxybutyric acid anilide was obtained.

EXAMPLES 250–274

The procedure of Example 3 was repeated with the organisms listed in Table 2 except that γ-bromoacetoanilide (1 mg/ml) was used as the substrate. Conversion to the desired (+)4-bromo-3(R)-hydroxybutyric acid anilide was obtained.

EXAMPLES 275–294

The procedure of Example 1 was repeated with the organisms listed in Table 1 except that γ-hydroxyacetoacetic octyl ester (1 mg/ml) was used as the substrate. Conversion to the desired 4-hydroxy-3(R)-hydroxybutyric acid octyl ester was obtained.

EXAMPLES 295–319

The procedure of Example 3 was repeated with the organisms listed in Table 2 except that γ-hydroxyacetoacetic octyl ester (1 mg/ml) was used as the substrate. Conversion to the desired 4-hydroxy-3(R)-hydroxybutyric acid octyl ester was obtained.

EXAMPLES 320–339

The procedure of Example 1 was repeated with the organisms listed in Table 1 except that γ-hydroxyacetoacetanilide (1 mg/ml) was used as the substrate. Conversion to the desired 4-hydroxy-3-(R)-hydroxybutyric acid anilide was obtained.

EXAMPLES 340–364

The procedure of Example 3 was repeated with the organisms listed in Table 2 except that γ-hydroxyacetoacetanilide (1 mg/ml) was used as the substrate. Conversion to the desired 4-hydroxy-3(R)-hydroxybutyric acid anilide was obtained.

General procedure for the conversion of 4-halo-3(R)-hydroxybutyric esters and amides into L-Carnitine chloride A mixture of 4-chloro-3(R)-hydroxybutyric acid octyl ester (1.5 g), ethanol (3 ml) and trimethylamine (25 wt % solution) in water (3 ml) was heated at 80°–90° C. for about 2 hours. The solvents and excess trimethylamine were evaporated to dryness in vacuo to yield 1.8 g of crude residue. The crude product (1 g) was heated at 80°–90° C. in a solution of 10% HCl (7 ml) for 1.5 hours. After evaporation of the solvents under reduced pressure, the crude product was extracted twice with absolute ethanol (10 ml) and the ethanol was evaporated in vacuo. The crystalline residue was dissolved in a small quantity of ethanol and the L-carnitine chloride was precipitated by the addition of ether in good yield (420 mg, 66%), m.p. 142° (dec.); [α] −23.7° (c, 4.5, H₂O).

The L-carnitine chloride can be readily converted to the pharmaceutically preferred L-carnitine inner salt by ion exchange means as is well known in the art.

TABLE 1 (YEASTS)

1. *Candida lipolytica* NRRL Y-1095
2. *Candida pseudotropicalis* NRRL Y-1264
3. *Mycoderma cerevisiae* NRRL Y-1615
4. *Torula lactosa* NRRL Y-329
5. *Geotrichum candidum* NRRL Y-552
6. *Hansenula anomal* NRRL Y-366
7. *Hansenula subpelliculosa* NRRL Y-1683
8. *Pichia alcoholophila* NRRL Y-2026
9. *Saccharomyces cerevisiae* NRRL Y-12,632

10. *Saccharomyces lactis* NRRL Y-1140
11. *Zygosaccharomyces priorianus* NRRL Y-12,624
12. *Saccharomyces acidifaciens* NRRL Y-7253
13. *Kloeckera corticis* ATCC 20109
14. *Cryptococos mascerans* ATCC 24194
15. *Rhodotorula sp.* ATCC 20254
16. *Candida albicans* ATCC 752
17. *Dipodascus albidus* ATCC 12934
18. *Saccharomyces cerevisiae* (commercial Red Star)
19. *Rhodotorula rubra* NRRL Y-1592
20. *Oospora lactis* ATCC 14318
   NRRL-Northern Regional Research Lab. at Peoria, Ill.
   ATCC-American Type Culture Collection at Rockville, Md.

TABLE 2 (FUNGI)

1. *Gliocladium virens* ATCC 13362
2. *Caldariomyces fumago* ATCC 16373
3. *Linderina pennisopora* ATCC 12442
4. *Aspergillus ochraceus* NRRL 405
5. *Trichoderma lignorum* ATCC 8678
6. *Heterocephalum autantiacum* ATCC 16328
7. *Entomophthora coronata* NRRL 1912
8. *Scopulariopsis constantini* NRRL 1860
9. *Zygorhynchus heterogamus* ATCC 6743
10. *Scopulariopsis brevicaulis* NRRL 2157
11. *Rhizopus arrhizus* NRRL 2286
12. *Penicillium thomii* NRRL 2077
13. *Mucor hiemalis* (-) NRRL 4088
14. *Byssochlamys nivea* ATCC 12550
15. *Penicillium patulum* NRRL 1952
16. *Metarrhizium anisopliae* ATCC 24942
17. *Penicillium islandicum* ATCC 10127
18. *Cunninghamella elegans* ATCC 1028a
19. *Cunninghamella echinulata* ATCC 11585a
20. *Asperigillus fumigatus* ATCC 16907
21. *Aspergillus amstelodami* NRRL 90
22. *Gliocladium roseum* ATCC 10521
23. *Aspergillus giganteus* ATCC 10059
24. *Absidia blakeleeana* ATCC 10148b
25. *Penicillium roqueforti* NRRL 849a

I claim:

1. A method for preparing optically active R-4-substituted-3-hydroxybutyric acid derivatives from a substrate consisting of corresponding 4-substituted acetoacetic acid esters or amides, wherein the ester or amide group comprises at least five carbon atoms, which comprises subjecting said 4-substituted acetoacetic acid esters or amides to the fermentative enzymatic action of a microorganism which elaborates oxido-reductase enzymes to cause the substrate to be converted to the desired R-4-substituted-3-hydroxybutyric acid derivative; and recovering the desired optically active R-4-substituted-3-hydroxybutyric acid derivatives.

2. The method of claim 1 wherein the microorganism is selected from the class Ascomycetes.

3. The method of claim 1 wherein the microorganism is selected from the orders Endomycetales, Mucorales, Moniliales or Eurotiales.

4. The method of claim 1 wherein the microorganism is selected from the genus Saccharomyces.

5. The method of claim 4 wherein the microorganism is *Saccharomyces cerevisiae*.

6. The method of claim 1 wherein the 4-substituted acetoacetic acid derivative subjected to fermentative enzymatic action is 4-chloro-acetoacetic acid octyl ester.

7. The method of claim 1 wherein the 4-substituted acetoacetic acid derivative subjected to fermentative enzymatic action is 4-chloro-acetoacetic acid benzyl ester.

8. The method of claim 1 wherein the 4-substituted acetoacetic acid derivative subjected to fermentative enzymatic action is 4-chloro-acetoacetanilide.

9. The method of claim 6 wherein the microorganism is *Saccharomyces cerevisiae*.

10. The method of claim 7 wherein the microorganism is *Saccharomyces cerevisiae*.

11. The method of claim 8 wherein the microorganism is *Saccharomyces cerevisiae*.

12. A method for preparing optically active R-4-substituted-3-hydroxybutyric acid derivatives which comprises subjecting compounds having the formula

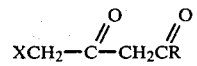

where X is selected from the group consisting of Cl, Br and OH and R is a hydrophobic unit containing at least five carbon atoms, in straight chain, branched chain or cyclic configuration, selected from the group consisting of: alkyl alcohol or amine groups having from about 5 to 15 carbon atoms, alicyclic alcohol or amine groups having from about 5 to about 12 carbon atoms, aromatic alcohols having from about 6 to about 14 carbon atoms, and aromatic amines selected from the group of formulas consisting of:

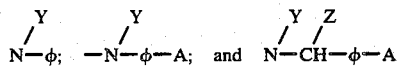

where Y and Z are selected from the group consisting of H, an alkyl group having from 1 to about 8 carbon atoms, phenyl, and benzyl and A is selected from the group consisting of H, CH$_3$, Cl and Br to the fermentative enzymatic action of a microorganism which elaborates oxido-reductase enzymes; and recovering the desired optically active R-4-substituted-3-hydroxybutyric acid derivatives from the fermentative reaction mixture.

13. The method of claim 12 wherein said aromatic alcohols contain as ring substituents H, CH$_3$, halo or nitro groups.

14. A method for preparing optically active R-4-substituted-3-hydroxybutyric acid derivatives from corresponding 4-substituted acetoacetic acid esters or amides wherein the ester or amide group includes at least five carbon atoms, which method comprises (a) subjecting said 4-substituted acetoacetic acid esters or amides to the fermentative enzymatic action of a microorganism selected from the group consisting of:
   *Candida lipolytica,*
   *Candida pseudotropicalis,*
   *Mycoderma cerevisiae,*
   *Torula lactosa,*
   *Geotrichum candidum,*
   *Hansenula anomala,*
   *Hansenula subpelliculosa,*
   *Pichia alcoholophila,*
   *Saccharomyces cerevisiae,*
   *Saccharomyces lactis,*
   *Zygosaccharomyces priorianus,*
   *Saccharomyces acidifaciens,*

Kloeckera corticis,
Cryptococcus mascerans,
Rhodotorula sp.,
Candida albicans,
Dipodascus albidus,
Rhodotorula rubra,
Oospora lactis,
Gliocladium virens,
Caldariomyces fumago,
Linderina pennisopora,
Aspergillus ochraceus,
Trichoderma lignorum,
Heterocephalum aurantiacum,
Entomophthora coronata,
Scopulariopsis constantini,
Zygorhynchus heterogamus,
Scopulariopsis brevicaulis,
Rhizopus arrhizus,
Penicillium thomii,
Mucor hiemalis,
Byssochlamys nivea,
Penicillium patulum,
Metarrhizium anisopliae,
Penicillium islandicum,
Cunninghamella elegans,
Cunninghamella echinulata,
Asperigillus fumigatus,
Aspergillus amstelodami,
Gliocladium roseum,
Aspergillus giganteus,
Absidia blakeleeana, and
Penicillium roqueforti; and (b) recovering the desired R-4-substituted-3-hydroxybutyric acid derivative from the fermentative reaction mixture.

15. The method of claim 14 wherein the 4-substituted acetoacetic acid esters or amides are compounds having the formula:

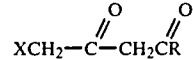

where X is selected from the group consisting of Cl, Br, and OH and, R is a hydrophobic moiety containing at least five carbon atoms and is selected from the group consisting of alkyl alcohol or amine groups having from about five to fifteen carbon atoms, alicylic alcohol or amine groups having from about five to about twelve carbon atoms, aromatic alcohols having from about six to about fourteen carbon atoms, and aromatic amines selected from the group of formulas consisting of:

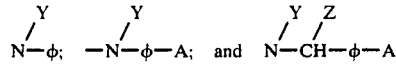

where Y and Z are selected from the group consisting of H, an alkyl group having from one to about eight carbon atoms, phenyl, and benzyl, and A is selected from the group consisting of H, $CH_3$, Cl, and Br.

16. The method of claim 15 wherein said aromatic alcohols contain as ring substitutents H, $CH_3$, halo or nitro groups.

* * * * *